(12) United States Patent
Yoshikawa et al.

(10) Patent No.: US 9,434,924 B2
(45) Date of Patent: Sep. 6, 2016

(54) CELL CULTURE METHOD AND CELL CULTURE KIT

(75) Inventors: Yoshihiro Yoshikawa, Osaka (JP); Naomi Morikawa, Osaka (JP); Ryo Tomii, Osaka (JP)

(73) Assignee: Nipro Corporation, Osaka (JP)

( * ) Notice: Subject to any disclaimer, the term of this patent is extended or adjusted under 35 U.S.C. 154(b) by 0 days.

(21) Appl. No.: 14/113,050

(22) PCT Filed: Apr. 20, 2012

(86) PCT No.: PCT/JP2012/060772
§ 371 (c)(1),
(2), (4) Date: Nov. 25, 2013

(87) PCT Pub. No.: WO2012/144624
PCT Pub. Date: Oct. 26, 2012

(65) Prior Publication Data
US 2014/0087465 A1    Mar. 27, 2014

(30) Foreign Application Priority Data

Apr. 21, 2011   (JP) .................................. 2011-094703

(51) Int. Cl.
| | | |
|---|---|---|
| C12N 5/077 | (2010.01) | |
| C12M 1/00 | (2006.01) | |
| C12M 1/26 | (2006.01) | |

(52) U.S. Cl.
CPC ............ *C12N 5/0656* (2013.01); *C12M 23/14* (2013.01); *C12M 33/00* (2013.01); *C12N 2509/10* (2013.01)

(58) Field of Classification Search
None
See application file for complete search history.

(56) References Cited

U.S. PATENT DOCUMENTS

| | | | |
|---|---|---|---|
| 4,937,194 A | 6/1990 | Pattillo | |
| 7,655,393 B2 | 2/2010 | Hasumi et al. | |
| 8,075,882 B2 | 12/2011 | Hasumi et al. | |
| 2005/0106717 A1* | 5/2005 | Wilson et al. | 435/297.5 |
| 2007/0286847 A1 | 12/2007 | Hasumi et al. | |
| 2010/0092445 A1 | 4/2010 | Hasumi et al. | |
| 2012/0141975 A1* | 6/2012 | Sato et al. | 435/2 |

FOREIGN PATENT DOCUMENTS

| | | | |
|---|---|---|---|
| EP | 1 757 680 | 2/2007 | |
| JP | 3-65177 | 3/1991 | |
| JP | 3-160984 | 7/1991 | |
| JP | 6-98756 | 4/1994 | |
| JP | 2006-262876 | 10/2006 | |
| JP | 2007-161589 | 6/2007 | |
| JP | 2007-330108 | 12/2007 | |
| JP | 2008-017839 | 1/2008 | |
| JP | 2009-136156 | 6/2009 | |
| WO | WO-2005/108554 | 11/2005 | |
| WO | WO 2009/099552 | * 8/2009 | ............... C12Q 1/04 |
| WO | WO-2011/047289 | 4/2011 | |

OTHER PUBLICATIONS

Sigma Trypsin Product Information, retrieved from the Internet, Feb. 17, 2015:http://www.thomassci.com/Chemicals/Reagent-T/_/9c012447-38f9-4c07-b8b0-f6d1ce13470d.*
UMBC, Tissue Culture Methods, 2010, retrieved from the Internet: http://userpages.umbc.edu/~jwolf//method5.htm.*
Vogel et al: "Effects of hyaluronidase, trypsin, and EDTA on surface composition and topography during detachment of cells in culture", Experimental Cell Research, Academic Press, US, vol. 113, No. 2, May 1, 1978, pp. 345-4827, DOI: 10.1016/0014-4827(78)90375-0 [retrieved on May 1, 1978] p. 345-357, right-hand column, paragraph 3—p. 354, right-hand column, paragraph 1.
Nagase K et al: "Temperature-responsive intelligent interfaces for blomolecular separation and cell sheet engineering" Journal of the Royal Society, Interface, The Royal Society, London, GB, vol. 6, No. Suppl. 3, Jun. 6, 2009, pp. S293-S309, XP002604260, ISSN: 1742-5689, DOI: 10.1098/RSIF.2008-0499.FOCUS [retrieved on Mar. 25, 2009] p. S301-p. S303.
Lachmann K et al: "Tailor-Made Surface Coatings for Cell Cultivation in a Closed Plastic Bag System", 19th International Symposium on Plasma Chemistry Bochum, Germany, Jul. 26-31, 2009. Jul. 26, 2009, pp. 1-4, XP002540535, Retrieved from the Internet: URL:http://www.ispc-conference.org/ispcproc/papers/360.pdf p. 1, left-hand column page 3, right-hand column, paragraph 2-paragraph 3.
"VueLife FEP Bag, Catalog No. 32-AC (Adherent Culture)", Internet Citation, Oct. 2, 2009, p. 1, XP002599553, Retrieved from the Internet: URL:http://www.cellgenix.com/ex-vivo-therapeutics/pdf/DataSheets/bags/VueLife_AC_32-ac.pdf [retrieved on Sep. 7, 2010] the whole document.
Macke Lars et al: "Evaluating maturation and genetic modification of human dendritic cells in a new polyolefin cell culture bag system", Transfusion, American Association of Blood Banks, Bethesda, MD, US, vol. 50, No. 4, Apr. 1, 2010, pp. 843-855, XP002599554, ISSN: 0041-1132, DOI: 10.1111/J.1537-2995.2009.02520.X [retrieved on Dec. 10, 2009] the whole document.
Supplementary European Search Report dated Oct. 28, 2014 (pp. 1-4).

* cited by examiner

*Primary Examiner* — Thane Underdahl
*Assistant Examiner* — Yvonne Pyla
(74) *Attorney, Agent, or Firm* — Jordan and Koda PLLC

(57) ABSTRACT

Provided is a means suitable for mass culture of adherent cells and which allows easy and safe collection of the cultured adherent cells. A cell culture kit has a culture bag having flexibility, such a level of hydrophilicity that the culture of adherent cells can be achieved, and permeability into a bag shape and which is filled with a culture medium; a dissociation solution bag filled with a dissociation solution containing a metal chelating agent or ornithine or a derivative thereof, and a solution sending circuit or a derivative thereof, and a solution sending circuit which connects the culture bag and the dissociation solution bag to each other and can send the dissociation solution from the dissociation solution bag to the culture bag.

6 Claims, 3 Drawing Sheets

Ex.1　　　　　Ex.2　　　　　Ex.3

Comp. Ex.1　　　　Ref. Ex.1　　　　Ref. Ex.2

Ex.1　　　　　Ex.2　　　　　Ex.3

Cells were not collected.

Comp. Ex.1　　　　Ref. Ex.1　　　　Ref. Ex.2

Ex.1

Ex.2

Ex.3

Comp. Ex.1

Ref. Ex.1

Ref. Ex.2

CELL CULTURE METHOD AND CELL CULTURE KIT

TECHNICAL FIELD

The present invention relates to a cell culture method and a cell culture kit for culturing adherent cells.

BACKGROUND OF THE INVENTION

Heretofore, a method of culturing adherent cells and suspension cells of mammals in vitro is known. Such culture has been performed in culture vessels typified by a flask and a Petri dish formed with glass or synthetic resin, for example. In general, many of such culture vessels have a small capacity, and thus are not suitable for mass culture.

On the other hand, a bag-shaped cell culture vessel has been devised as a vessel for culturing floating cells (Patent Literatures 1 to 3). In the cell culture vessel, a sealed space capable of sealing a culture medium by bonding synthetic resin sheets to each other is formed thereinside. A culture medium and a cell floating liquid can be made to flow into/out of the sealed space through a port. Moreover, a bag-shaped cell culture vessel suitable for culture of adherent cells has also been devised (Patent Literature 4).

CITATION LIST

Patent Literature

PTL 1: Japanese Unexamined Patent Application Publication No. 3-65177
PTL 2: Japanese Unexamined Patent Application Publication No. 3-160984
PTL 3: Japanese Unexamined Patent Application Publication No. 6-98756
PTL 4: Japanese Unexamined Patent Application Publication No. 2008-17839

SUMMARY OF THE INVENTION

For example, after adherent cells are cultured in a culture vessel, such as a flask and a Petri dish, an operation of dissociating the adherent cells from the inner surface of the culture vessel is required. For such an operation of dissociating the adherent cells, an instrument referred to as a cell scraper is used. In this operation, a technique of scraping the adherent cells from the inner surface of the culture vessel and a technique of dissociating the adherent cells from the inner surface of the culture vessel with a liquid containing protease, such as trypsin, are adopted.

However, in the dissociation of the adherent cells by a cell scraper, the strength (force) of scraping the inner surface of the culture vessel is applied to the adherent cells. Thus, there is a possibility that collapse and deformation of the adherent cells may occur. Moreover, the cell culture vessel is required to have an opening of a size which allows the cell scraper to reach the inner surface. For example, when the opening is small as in a narrow-mouthed flask, there are problems in that it has been difficult to make the cell scraper reach the entire region of the inner surface or the workability has deteriorated. Moreover, it has been impossible to insert the cell scraper into a culture bag. Furthermore, when performing mass culture using a Petri dish, tens to hundreds of Petri dishes are required to use. Therefore, it has been complicated to subject all of such a large amount of Petri dishes to the operation by the cell scraper.

On the other hand, the operation of dissociating the adherent cells from the inner surface of the culture vessel using the liquid containing protease is free from the problems that the operation is limited by the size of the opening of the culture vessel and the operation in mass culture is complicated as in the operation by the cell scraper. Therefore, the operation method can be utilized for, for example, a culture bag. However, trypsin treatment decomposes not only protein involved in cell adhesion but a cell membrane, and therefore cells may be damaged. Moreover, in the case where the protease, such as trypsin, is derived from animals, such as a pig, when the cultured adherent cells are used for regeneration medicine, there is a concern of the risk of virus contamination. On the other hand, there are problems in that inactivated protease and protease produced by recombinant are expensive.

The present invention has been made in view of the above-described circumstances. It is an object of the present invention to provide a means which is suitable for mass culture of adherent cells and which allows easy and safe collection of the cultured adherent cells.

(1) The present invention relates to a cell culture method of culturing adherent cells. The cell culture method according to the present invention includes a first process of holding a liquid culture medium in a culture bag which is formed by shaping at least one sheet having flexibility, such a level of hydrophilicity that the culture of adherent cells can be achieved, and permeability into a bag shape, and sowing adherent cells to the inner surface having hydrophilicity of the at least one sheet of the culture bag, and incubating the same, a second process of discharging the culture medium from the culture bag, and then filling the culture bag with a dissociation solution containing a metal chelating agent or ornithine or a derivative thereof, a third process of bending the at least one sheet of the culture bag filled with the dissociation solution to dissociate the adherent cells from the at least one sheet, and a fourth process of collecting the adherent cells dissociated from the at least one sheet of the culture bag.

In the first process, the adherent cells are cultured in the culture bag in the state where the adherent cells adhere to the inner surface of the at least one sheet of the culture bag. In the second process, the adherent cells are easily dissociated from the inner surface of the sheet by filling the culture bag with the dissociation solution. In this state, some of the adherent cells may be dissociated from the at least one sheet. In the third process, most of the adherent cells are dissociated from the at least one sheet by bending the sheet of the culture bag. In the fourth process, the dissociation solution containing the dissociated adherent cells are made to flow out of the culture bag, and then the adherent cells are collected.

(2) The dissociation solution may contain EDTA. Due to the fact that the dissociation solution contains EDTA, the adherent cells are more efficiently collected.

(3) In the third process, the at least one sheet of the culture bag may be bent at an environmental temperature lower than the environmental temperature of the culture bag in the incubation of the first process above.

Depending on the cell type, the shape of the adherent cells becomes a spherical shape due to the fact that the environmental temperature of the culture bag becomes low, so that the adherent cells are easily dissociated from the sheet.

(4) As the at least one sheet of the culture bag, one is mentioned which has a polyolefin resin layer at least on the inner surface side and which is imparted with hydrophilicity by subjecting the polyolefin resin layer to plasma treatment.

(5) The present invention may be regarded as a cell culture kit for culturing adherent cells. The cell culture kit according to the present invention has a first bag which is formed by shaping at least one sheet having flexibility, such a level of hydrophilicity that the culture of adherent cells can be achieved, and permeability into a bag shape and which is filled with a culture medium, a second bag which is filled with a dissociation solution containing a metal chelating agent or ornithine or a derivative thereof, and a solution sending circuit which connects the first bag and the second bag to each other and can send the dissociation solution from the second bag to the first bag.

According to the present invention, since the adherent cells are cultured using a culture bag, the invention is suitable for mass culture. Moreover, since the adherent cells are cultured on the inner surface of the flexible sheet, and then the sheet is bent in the state where the inner surface of the sheet is exposed to the dissociation solution, the adherent cells are dissociated from the sheet without applying excessive force to the adherent cells. Thus, the cultured adherent cells can be easily and safely collected.

EMBODIMENTS FOR CARRYING OUT THE INVENTION

Figure 1:
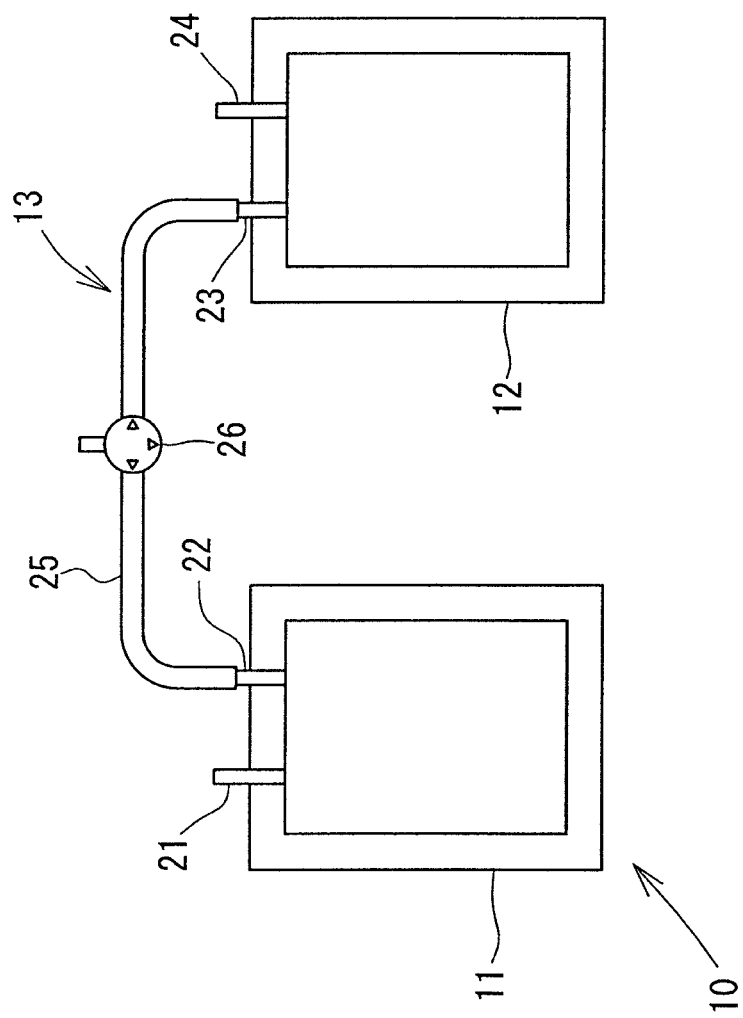
FIG. 1 is a perspective view illustrating the configuration of the appearance of a cell culture kit 10 according to an embodiment of the present invention.

The dissociation liquid contains a metal chelating agent or omithine or a derivative thereof. The dissociation solution does not contain trypsin. As the metal chelating agent, EDTA, NTA, DTPA, HIDS, citric acid, phytic acid, and the like are mentioned. Ornithine is one of the substances constituting a urea circuit, and is a kind of amino acids generated by decomposition of arginine. The molecular formula of ornithine is $C_5H_{12}N_2O_2$ and omithine is a compound referred to as 2,5-diaminopentanoic acid according to the IUPAC nomenclature. In the present invention, ornithine is a general term including all a racemic isomer, an L isomer, and a D isomer. In the present invention, L-ornithine is preferably used. Mentioned as a derivative of ornithine are N-[amino(hydroxyimino)methyl]-ornithine or a structural isomer, N-acetyl-omithine, N-acyl-omithine, N-(L-carboxyethyl)-omithine, N-succinyl-ornithine, N,N-dibenzoyl-omithine, (difluoromethyl)ornithine, N-[(hydroxy) (imino) methyl]-ornithine, and the like. As the metal chelating agent or ornithine or a derivative thereof, from the viewpoint that cells can be dissociated to some extent without bending the bag immediately after the dissociation solution treatment, it is preferable for the dissociation solution to at least contain ornithine or a derivative thereof. As the dissociation solution, it is particularly preferable to use a metal chelating agent or ornithine or a derivative thereof in combination from the viewpoint that the dispersion degree of the dissociated cells is good. Even in the case of a dissociation solution which does not contain ornithine and contains only a metal chelating agent, the cells are dissociated from the bag by bending the bag. Therefore, in the present invention, the dissociation solution is not always limited to one containing ornithine or a derivative thereof or one containing a metal chelating agent or ornithine or a derivative thereof in combination. The metal chelating agent or ornithine or a derivative thereof may be formed into the dissociation solution by, for example, being dissolved in a phosphate buffer. The pH of the phosphate buffer is set as appropriate according to the adherent cells to be cultured and the pH is preferably 7.2 to 7.4, for example. The dissociation solution may also contain a plurality of components of the metal chelating agent or ornithine or a derivative thereof. The dissociation solution may also contain other components, e.g., components having a cell dispersion action and a cytoprotective action, and the like. It is preferable for the dissociation solution not to contain calcium and magnesium. This is because the cells adhere by calcium-dependent protein and magnesium-dependent protein.

Hereinafter, a preferable embodiment of the present invention is described. The embodiment is simply one embodiment of the present invention and it is a matter of course that the embodiment can be altered insofar as the gist of the present invention is not changed.

As illustrated in FIG. 1, in the cell culture kit 10, a culture bag 11 and a dissociation solution bag 12 are connected by a solution sending circuit 13 in such a manner that a solution can be sent. The culture bag 11 is equivalent to the first bag. The dissociation solution bag 12 is equivalent to the second bag.

The culture bag 11 is a rectangular shape as viewed in plane, and can enclose a fixed capacity of a culture medium thereinside. The shape of the culture bag 11 is not particularly limited and the shape and the capacity are set in consideration of the capacity of a culture medium to fill the bag, the workability, and the like. When a sealed space for holding the culture medium is formed in the culture bag 11, a possibility that various germs and the like may enter the internal space of the culture bag 11 is reduced. The capacity of the culture bag 11 is preferably 20 to 1000 mL and is preferably 50 to 200 mL when workability is taken into consideration, for example.

The culture bag 11 is formed by bonding synthetic resin sheets having a rectangular shape as viewed in plane to each other. As a method of bonding the synthetic resin sheets to each other, a method of thermally fusing the periphery is mentioned, for example. On one edge side of the periphery, resin tubes 21 and 22 are disposed between the synthetic resin sheets. By the resin tubes 21 and 22, a port for making liquid flow into or flow out of the internal space of the culture bag 11 is formed. The number of the ports may be changed as appropriate. The resin tubes 21 and 22 can be opened and closed by a pinchcock, fusion, and the like.

The synthetic resin sheet constituting the culture bag 11 has flexibility and such a level of bending rigidity that the bag shape can be maintained. The flexibility and the bending rigidity of the synthetic resin sheet fluctuate depending on the raw materials, thickness, laminate structure, and the like. Therefore, by setting the selection of the raw materials, thickness, and laminate structure as appropriate, a synthetic resin sheet having desired flexibility and bending rigidity is obtained. Moreover, the synthetic resin sheet has gas permeability. Mentioned as the raw materials of such a synthetic resin sheet are, for example, low density polyethylene, ultrahigh molecular weight polyethylene, cyclic polyolefin resin, or a laminate structure thereof or with other materials.

When the laminate structure is adopted as the synthetic resin sheet, the inner surface side of the synthetic resin sheet is preferably a polyolefin resin layer from the viewpoint of reducing cytotoxicity. Mentioned as the polyolefin resin are low density polyethylene, middle density polyethylene, ultrahigh molecular weight polyethylene, a polyethylene-polytetrafluoroethylene copolymer, a polyethylene-1,2-dichloroethane copolymer, and the like.

Mentioned as the resin sheet to be laminated in the laminate structure are, for example, polyethylene, polyethyl acetate, polyvinyl alcohol, poly-1,2-dichloroethane, and the like. From the viewpoint of maintaining the shape of the synthetic resin sheet, polyethylene terephthalate, polyamide, and the like are mentioned. The laminate structure is not particularly limited and is preferably a laminate film of a three-layer structure containing a cyclic polyolefin polymer for the inner layer, polyethylene for the intermediate layer, and polyethylene terephthalate for the outer layer from the viewpoint of the cost of materials and manufacture and molding processability.

The polyolefin resin layer may be one containing a cyclic polyolefin polymer. The cyclic polyolefin polymer is a general term of polymers containing a cycloaliphatic hydrocarbon group (cyclic olefin monomer unit) in the molecules, is typified by one or more kinds of ring-opening polymers or addition polymers of cyclic olefin monomers, and is amorphous and has high transparency.

The type of the cyclic polyolefin polymer is not particularly limited and is preferably a ring-opening polymer because elution of a monomer and an oligomer hardly occurs and more preferably a hydrogenated ring-opening copolymer. The weight average molecular weight of the cyclic polyolefin polymer is not particularly limited and is preferably 5000 to 500000, more preferably 8000 to 250000, and still more preferably 10000 to 200000 from the viewpoint of the mechanical strength and the molding processability of a molded body (synthetic resin sheet).

The inner surface of the synthetic resin sheet has a cell adhesive functional group. The cell adhesive functional group refers to a chemical functional group excellent in compatibility with cells. Mentioned as the cell adhesive functional group are, for example, an amino group, an amine group, a hydroxyl group, a sulfone group, a sulfene group, a sulfine group, an ether group, a carboxyl group, a carbonyl group, and the like. Among the above, an amino group and a carboxyl group with high adhesiveness with cells are preferable. By the cell adhesive functional group, the inner surface of the synthetic resin sheet is rendered hydrophilic.

The polyolefin resin layer of the inner surface of the synthetic resin sheet is cell-adhesive functionalized by plasma treatment. The plasma treatment is treatment of electrically discharging under a specific gas atmosphere, and irradiating a treatment target with plasma generated by ionization action of specific gas to thereby give effects of etching, improvement of hydrophilicity (wettability), introduction of a functional group, and the like onto the surface of the treatment target. Mentioned as the electrical discharge in the plasma treatment are generally corona discharge (high pressure low temperature plasma), arc discharge (high pressure high temperature plasma), glow discharge (low pressure low temperature plasma), and atmospheric pressure plasma. Among the above, the atmospheric pressure plasma is preferable because the manufacturing cost is low.

The atmospheric pressure plasma is plasma treatment performed under atmospheric pressure and is usually performed under a pressure of $8.88 \times 10^{-2}$ to $10.85 \times 10^{-2}$ MPa. The other conditions are set as appropriate and, for example, the treatment is performed under the conditions where the temperature is in the range of about 25 to 50° C., the output is in the range of about 100 to 500 W, and the electrical discharge time is in the range of about 100 to 10000 seconds. The number of times the plasma treatment is not particularly limited and is usually about 1 to 10 times.

The specific gas to be used for the plasma treatment is arbitrarily selected by a person skilled in the art insofar as the gas at least contains an oxygen atom or a nitrogen atom. Mentioned as such specific gas are, for example, oxygen, nitrogen, air, carbon monoxide, carbon dioxide, nitrous oxide, ammonia, nitrogen trifluoride, and the like and mixed gas, such as oxygen/rare gas, nitrogen/rare gas, air/rare gas, carbon monoxide/rare gas, nitrous suboxide/rare gas, or nitrogen trifluoride/rare gas, and the like. Or, those in which liquid, such as water and hydrazine containing an oxygen element or a nitrogen element, is, vaporized may be acceptable. Furthermore, in addition to these gases, hydrogen, methane, carbon tetrafluoride, and the like may be contained in the specific gas insofar as the effects of the present invention are not impaired. Mentioned as the rare gas are, for example, helium, argon, neon, and xenon.

The plasma treatment may be performed to the synthetic resin sheet before being bonded as the culture bag 11 or after being formed into the culture bag 11. When subjecting the synthetic resin sheet to the plasma treatment, the peripheral region to be thermally fused is masked, and then the synthetic resin sheet can also be partially subjected to the plasma treatment.

For the plasma treatment, a plasma treatment apparatus is usually used. After the atmosphere of the inside of the chamber of the plasma treatment apparatus is rendered into a specific gas atmosphere, the synthetic resin sheet or the culture bag 11 is located between facing electrodes in the chamber, and electrical discharge is performed. Thus, the synthetic resin sheet or the culture bag 11 is subjected to the plasma treatment. Thereafter, the synthetic resin sheet or the culture bag 11 is extracted from the chamber.

The polyolefin resin layer is cell-adhesive functionalized by the plasma treatment, and cell adhesiveness (hydrophilicity) is given to the inner surface of the synthetic resin sheet. The effects of the plasma treatment can be evaluated as the contact angle of the inner surface of the synthetic resin sheet and water. From the viewpoint of the adhesiveness of cells, the contact angle of the inner surface of the synthetic resin sheet subjected to the plasma treatment is preferably 70° or less and more preferably 45° or less. The method of cell-adhesive functionalizing the polyolefin resin layer is not limited to the plasma treatment and the functionalization may also be carried out by, for example, irradiating the synthetic resin sheet with ion beams.

The inside of the culture bag 11 is filled with a liquid culture medium suitable for culturing adherent cells. As such a culture medium, MEM, DMEM, PRMI-1640, Ham F-12, and the like are mentioned, for example.

The dissociation solution bag 12 has a rectangular shape as viewed in plane and can enclose a fixed capacity of a dissociation solution thereinside. The shape of the dissociation solution bag 12 is not particularly limited and the shape and the capacity are set in consideration of the capacity of the dissociation solution to fill the bag, workability, and the like. Due to the fact that the dissociation solution bag 12 forms a sealed space for holding the dissociation solution, a possibility that various germs and the like may enter the internal space of the dissociation solution bag 12 is reduced. As the capacity of the dissociation solution bag 12, 20 to 400 mL is adopted, for example, and when the workability is taken into consideration, the capacity is preferably 50 to 200 mL.

The dissociation solution bag 12 is formed by bonding synthetic resin sheets having a rectangular shape as viewed in plane to each other. As a method of bonding the synthetic resin sheets to each other, a method of thermally fusing the periphery of the synthetic resin sheets is mentioned, for example. On one edge of the periphery of the synthetic resin sheets, resin tubes 23 and 24 are disposed between the synthetic resin sheets. By the resin tubes 23 and 24, a port for making liquid flow in or flow out of the internal space of the dissociation solution bag 12 is formed. The number of the ports may be changed as appropriate. The resin tubes 23 and 24 can be opened and closed by a pinchcock, fusion, and the like.

The dissociation solution bag 12 stores the dissociation solution, and therefore is not always required to have the same flexibility, bending rigidity, hydrophilicity, and gas permeability as those of the synthetic resin sheet as in the culture bag 11. In order to make the dissociation solution smoothly flow out of the dissociation solution bag 12, it is preferable for the dissociation solution bag 12 to have moderate flexibility.

DETAILED DESCRIPTION OF THE PREFERRED EMBODIMENTS

The solution sending circuit 13 has a tube 25 connected to the resin tube 22 of the culture bag 11 and the resin tube 23 of the dissociation solution bag 12 and a three-way cock 26 provided in the tube 25. The tube 25 is not particularly limited insofar as the tube allows the circulation of the dissociation solution and, for example, those containing the same raw materials as those of the resin tubes 22 and 23 are used. The three-way cock 26 is an example of a configuration for controlling the circulation state of the culture bag 11 and the dissociation solution bag 12 and may be replaced by a pinchcock or the like, for example.

Hereinafter, a cell culture method using the cell culture kit 10 is described. The cell culture kit 10 is used for culturing adherent cells. The adherent cell is a cell which adheres to a base material and can proliferate on the base material as the ground, and is a concept opposed to a floating cell. Mentioned as the adherent cells are, for example, periosteum cells, mesenchymal stem cells, nerve cells, epithelial cells, fibroblasts, embryonic stem cells (ES cells), induced pluripotent stem cells (iPS cells), and the like.

In this embodiment, the cell culture method according to the present invention is described as an aspect in which the cell culture kit 10 is used. However, it is a matter of course that the cell culture method according to the present invention is not limited to the aspect in which the cell culture kit 10 is used. Therefore, for example, an embodiment may be acceptable in which the culture bag 11 is filled with adherent cells and a cell suspension in a culture medium, a dissociation solution is separately prepared and is made to flow into the culture bag 11, and then the adherent cells are dissociated in the culture bag 11.

The cell culture method according to this embodiment is roughly divided into the following four processes.
(1) First process of sowing adherent cells to the inner surface of the culture bag 11, and incubating the same.
(2) Second process of discharging a culture medium from the culture bag 11, and filling the culture bag 11 with a dissociation solution.
(3) Third process of bending a synthetic resin sheet of the culture bag 11 filled with the dissociation solution, and dissociating the adherent cells from the synthetic resin sheet.
(4) Fourth process of collecting the adherent cells dissociated from the synthetic resin sheet of the culture bag 11.

In the first process, adherent cells to be cultured and a suspension (cell suspension) in a culture medium are injected from the resin tube 21 to the culture bag 11. The concentration of the adherent cells in the culture bag 11 is set as appropriate and is usually about 2000 to 3000 cells/cm$^2$ per unit area of the inner surface of the culture bag 11 as a standard. After injecting the cell suspension into the culture bag 11, the culture bag 11 is allowed to stand for about 10 to 40 minutes. Thus, the adherent cells in the cell suspension precipitate to adhere to the inner surface of the culture bag 11. More specifically, the adherent cells are sowed to the inner surface of the culture bag 11. When sowing the adherent cells to the both sides of the inner surface of the culture bag 11, the culture bag 11 is reversed in such a manner that the back surface and the front surface may be reversed thereafter, and then the adherent cells are made to adhere also to the inner surface of the opposite side. Then, incubation is performed under predetermined culture conditions, e.g., under a carbon dioxide environment, 37° C., and the like, for culturing the cells.

In the second process, first, the culture medium is made to flow out of the resin tube 21 of the culture bag 11. Since the adherent cells adhere to the inner surface of the culture bag 11, the adherent cells are not made to flow out with the culture medium. After discharging the culture medium, in order to remove culture medium components in the culture bag 11, the three-way cock 26 of the solution sending circuit 13 is opened to send the dissociation solution to the culture bag 11 from the dissociation solution bag 12. First, a certain amount of the dissociation solution is sent to the culture bag 11, and then the dissociation solution is made to flow out of the resin tube 21 of the culture bag 11. By repeating the process several times, the inner surface of the culture bag 11 is washed with the dissociation solution.

Thereafter, the culture bag 11 is filled with the dissociation solution, and then allowed to stand under an environment of normal temperature or 4° C. for several minutes to 1 hour. While being allowed to stand, the synthetic resin sheet of the culture bag 11 may be bent several times.

In the third process, the synthetic resin sheet is bent with the culture bag 11 in both hands. A method of bending the synthetic resin sheet of the culture bag 11 is not particularly limited. A method of lightly striking the culture bag 11, shaking the culture bag 11, or the like may be adopted. Due to the fact that the synthetic resin sheet is bent in the state where the inner surface of the culture bag 11 is exposed to the dissociation solution, the adherent cells are dissociated from the synthetic resin sheet. It is considered that, due to the fact that the culture bag 11 is placed under a low temperature environment, the shape of the adherent cells becomes a spherical shape, so that the adherent cells are easily dissociated from the synthetic resin sheet.

In the fourth process, the dissociation solution containing the adherent cells is made to flow out of the resin tube 21 of the culture bag 11, and then the cultured adherent cells are collected. Thereafter, the adherent cells are washed or prepared according to the purposes of use, such as regeneration medicine.

Thus, according to this embodiment, the adherent cells are cultured using the culture bag 11, and therefore the invention is suitable for mass culture. Moreover, since the adherent cells are cultured on the inner surface of the culture bag 11 and the synthetic resin sheet is bent in the state where the inner surface of the culture bag 11 is exposed to the dissociation solution, the adherent cells are dissociated from the synthetic resin sheet without applying excessive force to the adherent cells. Thus, the cultured adherent cells can be simply and safely collected.

EXAMPLES

Hereinafter, Examples of the present invention are described. Examples describe one embodiment of the present invention and it is a matter of course that the present invention is not limited to those described in Examples.

Example 1

A 250 μm thick resin sheet containing a low density polyethylene (LDPE, manufactured by Mitsubishi Pharma Chemicals, Co., Ltd.) monolayer was cut into a rectangle 100 mm long and 120 mm wide. About 10 mm of the peripheral region of the cut resin sheet was masked, and subjected to atmospheric pressure plasma treatment. The atmospheric pressure plasma treatment was performed at about 25° C. at atmospheric pressure under a mixed gas atmosphere of 68% by capacity of argon, 29% by capacity of helium, and 3% by capacity of nitrogen. A high-pressure electrode and a low-pressure electrode were formed into a plate shape (335 mm×250 mm) and the distance between the electrodes was set to 3 mm. A voltage of 2.2 kV was applied between the high-pressure electrode and the low-pressure electrode using an alternating current power supply having a frequency of 5 kHz as a power supply. By performing the plasma treatment for 30 seconds, a cell adhesive functional group was introduced into the central part (80 mm long×100 mm wide) of the resin sheet.

The same culture bag 11 as that of the embodiment described above was obtained by laminating two resin sheets subjected to plasma treatment, disposing a polyethylene tube as a port between films, and then fusing the peripheral region by heat sealing. The obtained culture bag 11 was subjected to sterilization using gamma rays. The inner surface of the culture bag 11 was analyzed using an FT-IR (Fourier transformed infrared spectrum) apparatus (Jasco, Product name: FT/IR-420) and an ultimate analysis apparatus (JEOL, JMS-6360LP), and then it was confirmed that the amino group is functionalized.

Into the culture bag 11 described above, embryo fibroblasts formed into a cell suspension by a DMEM culture medium containing 10% fetal bovine serum 1 was introduced, and then the cells were cultured under the conditions of 37° C. and saturated humidity. As a dissociation solution, a phosphate buffer containing 0.01% EDTA (metal chelating agent) and not containing calcium and magnesium was used. The culture medium was made to flow out of the culture bag 11, the inner surface of the culture bag 11 was washed with the dissociation solution, the culture bag 11 was filled with 50 ml of the dissociation solution, and then the culture bag 11 was allowed to stand at normal temperature for 10 minutes. After the culture bag 11 was lightly bent with both hands, the dissociation solution was collected from the culture bag 11, and then the number of adherent cells was counted.

Example 2

Example 2 was carried out in the same manner as in Example 1, except using 1% L-ornithine in place of the 0.01% EDTA (metal chelating agent).

Example 3

Example 3 was carried out in the same manner as in Example 1 using 0.01% EDTA (metal chelating agent) and 1% L-ornithine in place of the 0.01% EDTA (metal chelating agent).

Comparative Example 1

Adherent cells were cultured under the same conditions as those of Example 1, expect using a flask in place of the culture bag 11. Thereafter, 10 ml of a dissociation solution was made to flow into the flask, and allowed to stand for 10 minutes in the same manner as in Example 1. Thereafter, the dissociation solution was collected from the flask, and then the number of the adherent cells suspended in the dissociation solution was counted.

Reference Example 1

Adherent cells were cultured in the culture bag 11 in the same manner as in Example 1. Thereafter, 10 ml of a dissociation solution containing 0.25% trypsin (250 IU)-0.01% EDTA was made to flow into the culture bag 11, and then allowed to stand at 37° C. for 5 minutes. Thereafter, after bending the culture bag 11, the dissociation solution was collected from the culture bag 11, and then the number of the adherent cells suspended in the dissociation solution was counted.

Reference Example 2

Adherent cells were cultured under the same conditions as those of Example 1, except using a flask in place of the culture bag 11. Thereafter, 2 ml of a dissociation solution containing 0.25% trypsin (250 IU)-0.01% EDTA was made to flow into the flask, and then allowed to stand at 37° C. for 5 minutes. Thereafter, the dissociation solution was collected from the flask, and then the number of the adherent cells suspended in the dissociation solution was counted.

Table 1 shows the results when the number of the collected adherent cells was the number per unit area ($\times 10^4$ cells/cm$^2$) in Examples 1 to 3, Comparative Example 1, and Reference Examples 1 and 2, the recovery in Examples 1 to 3 when the recovery of Reference Example 1 was set to 100, and the recovery in Comparative Example 1 when the recovery of Reference Example 2 was set to 100.

TABLE 1

The number of the collected adherent cells per unit area and the recovery rate of the collected adherent cells.

|  | ×10$^4$ cells/cm$^2$ | Recovery (%) |
| --- | --- | --- |
| Ex. 1 | 2.6 | 84 |
| Ex. 2 | 2.2 | 70 |
| Ex. 3 | 3.0 | 97 |
| Comp. Ex. 1 | 0.07 | 2.8 |
| Ref. Ex. 1 | 3.1 | 100 |
| Ref. Ex. 2 | 2.53 | 100 |

Figure 2:
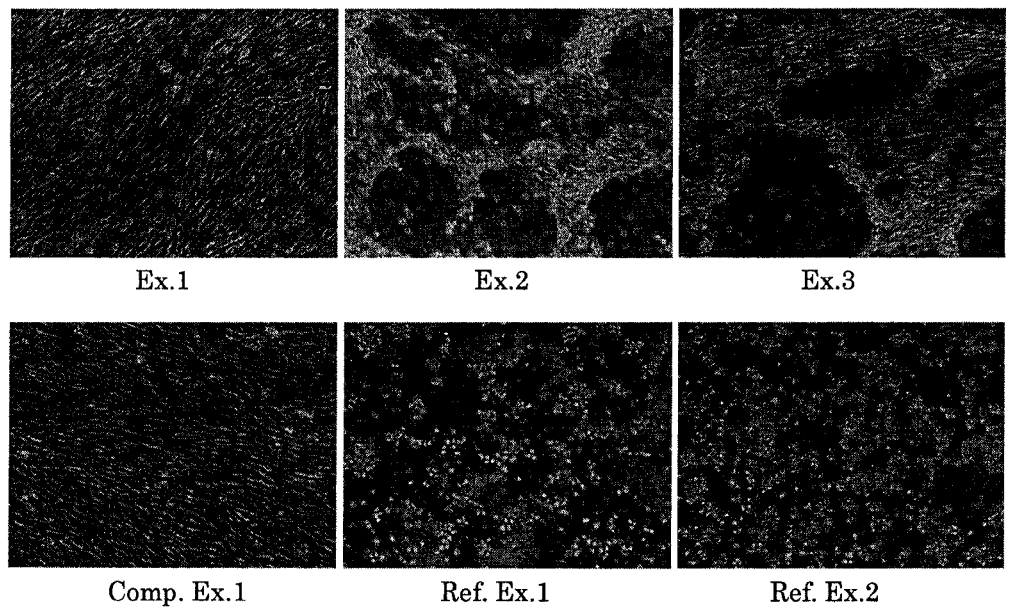
FIG. 2 are microphotographs in which a portion where cells are cultured in a vessel immediately after treating a dissociation solution (a bag is not bent) was observed in Examples 1 to 3, Comparative Example 1, and Reference Examples 1 and 2 of the present invention.

FIG. 2 show photographs in which portions where the cells were cultured in the suspicion (the culture bag 11 or the flask, before bending the culture bag 11) immediately after the dissociation solution treatment were observed under a microscope in Examples 1 to 3, Comparative Example 1, and Reference Examples 1 and 2. FIG. 2 show that the cells adhered to the vessel in Example 1 and Comparative Example 1 but, in Example 1, the cells were dissociated by bending the culture bag 11. On the other hand, some of the cells adhered in Examples 2 and 3 but some of the cells were dissociated without bending the culture bag 11. This shows that it is preferable for the dissociation solution to at least contain ornithine or a derivative thereof. In Reference Examples 1 and 2, since trypsin was contained in the dissociation solution, the cells were dissociated from the vessel even immediately after treating the vessel with the dissociation solution.

Figure 3:
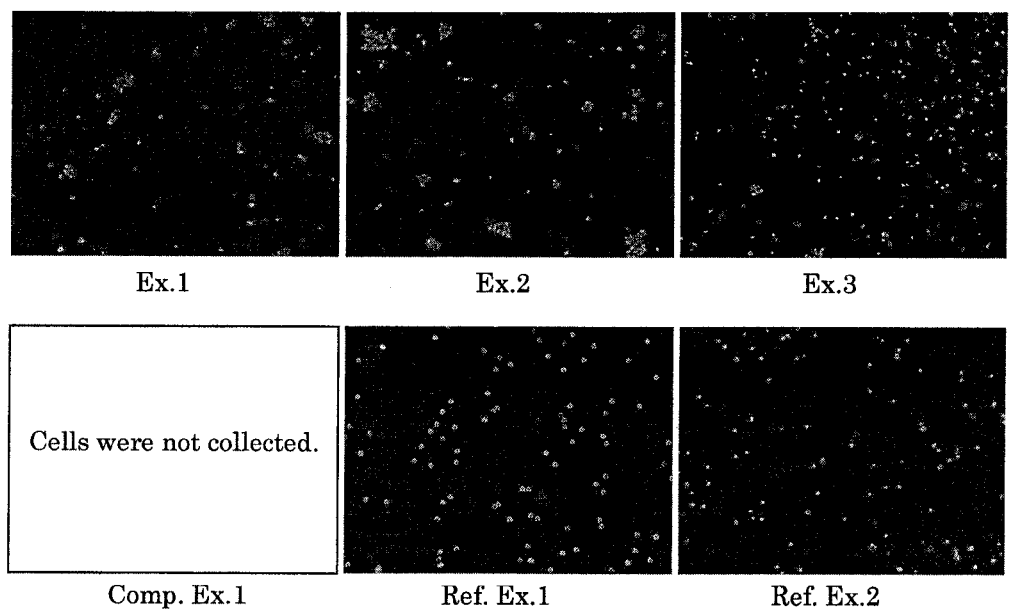
FIG. 3 are microphotographs in which the state of cells suspended in a dissociation solution after collection was observed in Examples 1 to 3, Comparative Example 1, and Reference Examples 1 and 2 of the present invention.

FIG. 3 show photographs in which the state of the cells suspended in the dissociation solution after treating the vessel with the dissociation solution, and then bending the culture bag 11 when the vessel was the culture bag 11 was observed under a microscope in Examples 1 to 3, Comparative Example 1, and Reference Examples 1 and 2. It was confirmed from FIG. 3 that an aggregation mass of the cells was partially observed in Examples 1 and 2. On the other hand, the cells suspended in the dissociation solution were dispersed in Example 3. This shows that it is particularly preferable to use a metal chelating agent or ornithine or a derivative thereof in combination as the dissociation solution. In Reference Examples 1 and 2, since trypsin was contained in the dissociation solution, the cells suspended in the dissociation solution were dispersed. In Comparative Example 1, since the cells were not dissociated, the cells were not able to be observed in the dissociation solution.

Figure 4:
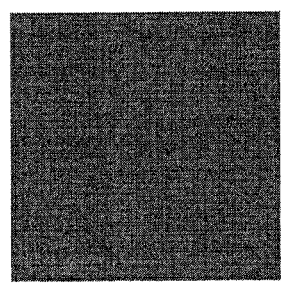
FIG. 4 are photographs in which cells adhering to a vessel after collection were subjected to Giemsa staining in Examples 1 to 3, Comparative Examples 1, and Reference Examples 1 and 2 of the present invention.
Figure 4:
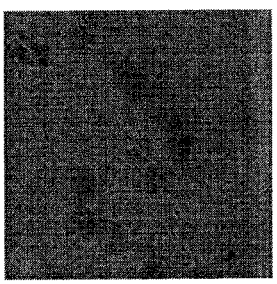
Figure 4:
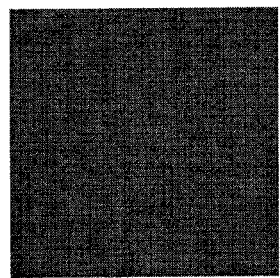
Figure 4:
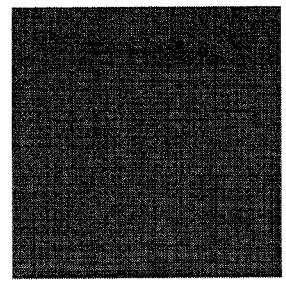
Figure 4:
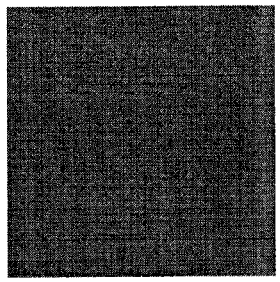
Figure 4:
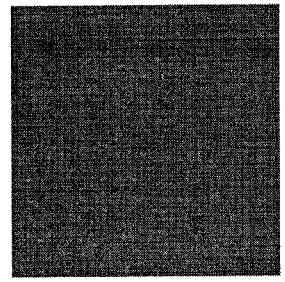

FIG. 4 show photographs in which the cells adhering to the vessel (the bag or the flask, after bending the bag) after the collection were subjected to Giemsa staining (The cells were dyed purple.) in Examples 1 to 3, Comparative Example 1, and Reference Examples 1 and 2. It was confirmed from FIG. 4 that since the vessel was dyed purple only in Comparative Example 1, the cells adhered (remained) to the vessel. On the other hand, it was confirmed in Examples 1 to 3 and Reference Examples 1 and 2 that the vessel was not dyed and almost all of the cells were able to be collected.

As is clear from the number of the collected cells of Examples 1 to 3, Comparative Example 1, and Reference Examples 1 and 2, according to Examples 1 to 3, the adherent cells were collected with the same efficiency as that of the dissociation of the adherent cells by trypsin which was used heretofore as in Reference Examples 1 and 2. A comparison between Reference Example 2 and Comparative Example 1 showed that, with the vessel not having flexibility as in the flask, the collection of the cells is difficult unless trypsin is used. It was confirmed from a comparison between Example 1 and Comparative Example 1, even when the same dissociation solution is used, the cells are hardly collected in Comparative Example 1 but, by using the culture bag 11, and bending the synthetic resin sheet as in Examples 1 to 3, almost all of the cells can be collected.

REFERENCE SIGNS LIST

10 Cell culture kit
11 Culture bag (First bag)
12 Dissociation solution bag (Second bag)
13 Solution sending circuit

The invention claimed is:

1. A cell culture method of culturing adherent cells, comprising:
holding a liquid culture medium in a culture bag which is formed by shaping at least one sheet having flexibility and permeability into a bag shape, the sheet having an inner cell-contacting surface having hydrophilicity sufficient to promote a culture of cells that adhere to the inner cell-contacting surface, whereby upon sowing, the cells adhere directly to the inner cell-contacting surface having hydrophilicity;
incubating the cells;
discharging the culture medium from the culture bag, and then filling the culture bag with a dissociation solution which does not contain trypsin, the dissociation solution containing ornithine or a derivative of ornithine selected from N-[amino(hydroxyimino)methyl]-ornithine or a structural isomer thereof, N-acetyl-ornithine, N-acyl-ornithine, N-(L-carboxyethyl)-ornithine, N-succinyl-ornithine, N,N-dibenzoyl-ornithine, (difluoromethyl)ornithine and N-[(hydroxy) (imino) methyl]-ornithine, the dissociation solution filling the culture bag through a solution sending circuit which connects the culture bag and a bag holding the dissociation solution to each other;
bending the at least one sheet of the culture bag filled with the dissociation solution to dissociate the adherent cells from the inner cell-contacting surface; and
collecting the adherent cells dissociated from the inner cell-contacting surface.

2. The cell culture method according to claim 1, wherein the dissociation solution further contains EDTA.

3. The cell culture method according to claim 1, wherein in the step of bending the at least one sheet, the sheet is bent at an environmental temperature lower than an environmental temperature of the culture bag during said incubating.

4. The cell culture method according to claim 1, wherein the sheet of the culture bag comprises a polyolefin resin layer on the inner cell-contacting surface that is imparted with hydrophilicity by subjecting the polyolefin resin layer to plasma treatment.

5. The cell culture method according to claim 1, wherein the sheet of the culture bag comprises polyolefin resin layer that includes a cyclic polyolefin polymer on at least the inner cell-contacting surface that is imparted with hydrophilicity by subjecting the polyolefin resin layer to plasma treatment.

6. The cell culture method according to claim 1, the inner cell-contacting surface is comprised of a synthetic resin layer having a cell-adhesive functional group.

* * * * *